United States Patent
Williams et al.

(10) Patent No.: US 6,596,239 B2
(45) Date of Patent: Jul. 22, 2003

(54) ACOUSTICALLY MEDIATED FLUID TRANSFER METHODS AND USES THEREOF

(75) Inventors: Roger O. Williams, Paradise Valley, AZ (US); Tarlochan Singh, Santa Clara, CA (US); N. Nicolas Mansour, Hillsborough, CA (US); Lawrence Lee, Jr., Sunnyvale, CA (US); Michael J. Forbush, Hollister, CA (US)

(73) Assignee: EDC Biosystems, Inc., San Jose, CA (US)

( * ) Notice: Subject to any disclaimer, the term of this patent is extended or adjusted under 35 U.S.C. 154(b) by 35 days.

(21) Appl. No.: 09/735,709

(22) Filed: Dec. 12, 2000

(65) Prior Publication Data

US 2002/0094582 A1 Jul. 18, 2002

(51) Int. Cl.[7] ................................................. B01L 3/02
(52) U.S. Cl. ........................................ 422/100; 347/46
(58) Field of Search .......................... 422/100; 347/46; 73/863–864.91

(56) References Cited

U.S. PATENT DOCUMENTS

| | | | |
|---|---|---|---|
| 3,903,990 A | * | 9/1975 | Tannaka ..................... 181/176 |
| 4,225,951 A | | 9/1980 | Menin et al. |
| 4,308,547 A | | 12/1981 | Lovelady et al. |
| 4,385,255 A | | 5/1983 | Yamaguchi et al. |
| 4,493,795 A | | 1/1985 | Nestor, Jr. et al. |
| 4,605,009 A | | 8/1986 | Pourcelot et al. |
| 4,697,195 A | | 9/1987 | Quate et al. |
| 4,719,476 A | | 1/1988 | Elrod et al. |

(List continued on next page.)

FOREIGN PATENT DOCUMENTS

| | | |
|---|---|---|
| EP | 0 549 244 B1 | 6/1993 |
| EP | 0 845 357 A2 | 6/1998 |
| EP | 0 845 357 A3 | 6/1998 |
| WO | WO 02/24323 | 3/2002 |
| WO | WO 02/24324 A2 | 3/2002 |
| WO | WO 02/24325 | 3/2002 |
| WO | WO 02/26394 | 4/2002 |
| WO | WO 02/26756 | 4/2002 |
| WO | WO 02/44319 | 6/2002 |
| WO | WO 02/47075 | 6/2002 |
| WO | WO 02/066713 | 8/2002 |

OTHER PUBLICATIONS

Avrameas, S. et al., (1978) "Coupling of enzymes to antibodies and antigens" *Scandinavia J. of Immunol.* 8(Suppl. 7):7–23.

DeLuca, D. (1982) "Chapter 7: Immunofluorescence Analysis" *Antibody as a Tool*, The Application of Immunochemistry, Marchalonis, J.J. et al., eds., John Wiley & Sons, Ltd., pp. 189–231.

Galfré, G. et al., (1981) "Preparation of monoclonal antibodies: strategies and procedures" *Methods in Enzymology* 73:3–46.

(List continued on next page.)

*Primary Examiner*—Jill Warden
*Assistant Examiner*—Elizabeth Quan
(74) *Attorney, Agent, or Firm*—Morrison & Foerster LLP

(57) ABSTRACT

Acoustic waves are used to transfer small amounts of fluid in a non-contact manner. Acoustic waves are propagated through a pool of a source fluid in such a manner that causes the ejection of a single micro-droplet from the surface of the pool. The droplet is ejected towards a target with sufficient force to provide contact of the droplet with the target. Because the fluid is not contacted by any fluid transfer device such as a pipette, the opportunities for contamination are minimized. Methods may be employed to transfer fluids from an array of source sites to an array of target sites, thereby enabling the precise automation of a wide variety of procedures including screening and synthesis procedures commonly used in biotechnology.

47 Claims, 5 Drawing Sheets

U.S. PATENT DOCUMENTS

| | | |
|---|---|---|
| 4,719,480 A | 1/1988 | Elrod et al. |
| 4,745,419 A | 5/1988 | Quate et al. |
| 4,748,461 A | 5/1988 | Elrod |
| 4,749,900 A | 6/1988 | Hadimioglu et al. |
| 4,751,529 A * | 6/1988 | Elrod et al. .................... 347/46 |
| 4,751,530 A | 6/1988 | Elrod et al. |
| 4,751,534 A | 6/1988 | Elrod et al. |
| 4,782,350 A | 11/1988 | Smith et al. |
| 4,797,693 A | 1/1989 | Quate |
| 4,801,950 A | 1/1989 | Frehling |
| 4,801,953 A * | 1/1989 | Quate .......................... 347/46 |
| 4,867,517 A | 9/1989 | Rawson |
| 4,959,674 A | 9/1990 | Khri-Yakub et al. |
| 5,028,937 A | 7/1991 | Khuri-Yakub et al. |
| 5,041,849 A | 8/1991 | Quate et al. |
| 5,070,488 A | 12/1991 | Fukushima et al. |
| 5,074,649 A | 12/1991 | Hamanaka |
| 5,087,931 A | 2/1992 | Rawson |
| 5,111,220 A | 5/1992 | Hadimioglu et al. |
| 5,115,809 A | 5/1992 | Saitoh et al. |
| 5,121,141 A | 6/1992 | Hadimoglu et al. |
| 5,122,818 A | 6/1992 | Elrod et al. |
| 5,142,307 A | 8/1992 | Elrod et al. |
| 5,163,436 A | 11/1992 | Saitoh et al. |
| 5,176,140 A | 1/1993 | Kami et al. |
| 5,191,354 A | 3/1993 | Quate |
| 5,194,880 A | 3/1993 | Elrod et al. |
| 5,216,451 A | 6/1993 | Rawson et al. |
| 5,229,793 A | 7/1993 | Hadimioglu et al. |
| 5,231,426 A | 7/1993 | Sweet |
| 5,268,610 A | 12/1993 | Hadimioglu et al. |
| 5,278,028 A | 1/1994 | Hadimioglu et al. |
| 5,287,126 A | 2/1994 | Quate |
| 5,299,578 A | 4/1994 | Rotteveel et al. |
| 5,305,016 A | 4/1994 | Quate |
| 5,339,101 A | 8/1994 | Rawson et al. |
| 5,379,865 A | 1/1995 | Berdich et al. |
| 5,389,956 A | 2/1995 | Hadimioglu et al. |
| 5,428,381 A | 6/1995 | Hadimioglu et al. |
| 5,450,107 A | 9/1995 | Rawson |
| 5,504,564 A | 4/1996 | Snelling et al. |
| 5,520,715 A | 5/1996 | Oeftering |
| 5,541,627 A | 7/1996 | Quate |
| 5,565,113 A * | 10/1996 | Hadimioglu et al. .......... 216/2 |
| 5,589,864 A | 12/1996 | Hadimioglu |
| 5,591,490 A | 1/1997 | Quate |
| 5,608,433 A | 3/1997 | Quate |
| 5,612,723 A | 3/1997 | Shimura et al. |
| 5,629,724 A | 5/1997 | Elrod et al. |
| 5,631,678 A | 5/1997 | Hadimioglu et al. |
| 5,669,389 A | 9/1997 | Rotteveel et al. |
| 5,669,971 A | 9/1997 | Bok et al. |
| 5,686,945 A | 11/1997 | Quate et al. |
| 5,692,068 A | 11/1997 | Bryenton et al. |
| 5,709,737 A | 1/1998 | Malhotra et al. |
| 5,722,479 A | 3/1998 | Oeftering |
| 5,798,779 A * | 8/1998 | Nakayasu et al. ............ 347/46 |
| 5,808,636 A | 9/1998 | Stearns |
| 5,810,009 A | 9/1998 | Mine et al. |
| 5,821,958 A | 10/1998 | Lim |
| 5,877,800 A | 3/1999 | Robinson et al. |
| 5,912,679 A | 6/1999 | Takayama et al. |
| 6,003,388 A | 12/1999 | Oeftering |
| 6,007,183 A | 12/1999 | Horine |
| 6,015,880 A | 1/2000 | Baldeschwieler et al. |
| 6,019,814 A | 2/2000 | Horine |
| 6,029,518 A | 2/2000 | Oeftering |
| 6,038,752 A | 3/2000 | Finsterwald et al. |
| 6,048,050 A | 4/2000 | Gundlach et al. |
| 6,134,291 A * | 10/2000 | Roy et al. ..................... 377/46 |
| 6,136,210 A | 10/2000 | Biegelsen et al. |
| 6,142,618 A | 11/2000 | Smith et al. |
| 6,154,236 A | 11/2000 | Roy et al. |
| 6,159,013 A | 12/2000 | Parienti |
| 6,187,211 B1 | 2/2001 | Smith et al. |
| 6,200,491 B1 | 3/2001 | Zesch et al. |
| 6,299,272 B1 | 10/2001 | Baker et al. |
| 6,312,121 B1 * | 11/2001 | Smith et al. .................. 347/96 |
| 6,336,696 B1 | 1/2002 | Ellson et al. |
| 2002/0037359 A1 | 3/2002 | Mutz et al. |
| 2002/0037375 A1 | 3/2002 | Ellson et al. |
| 2002/0037527 A1 | 3/2002 | Ellson et al. |
| 2002/0037579 A1 | 3/2002 | Ellson et al. |
| 2002/0042077 A1 | 4/2002 | Ellson |
| 2002/0061258 A1 * | 5/2002 | Mutz et al. ................... 422/53 |
| 2002/0061598 A1 | 5/2002 | Mutz et al. |
| 2002/0064808 A1 | 5/2002 | Mutz et al. |
| 2002/0064809 A1 | 5/2002 | Mutz et al. |
| 2002/0085063 A1 * | 7/2002 | Mutz et al. ................... 347/46 |
| 2002/0086319 A1 | 7/2002 | Ellson et al. |
| 2002/0090720 A1 | 7/2002 | Mutz et al. |
| 2002/0142286 A1 | 10/2002 | Mutz et al. |
| 2002/0155231 A1 | 10/2002 | Ellson et al. |

OTHER PUBLICATIONS

Mandenius, C.F. et al. (1986) "Reversible and specific interaction of dehydrogenases with a coenzyme–coated surface continuously monitored with a reflectometer" *Anal. Biochem.* 157:283–288.

Rodwell, J.D. (1985) "Linker Technology: Antibody–mediated delivery systems" *Biotech.*, 3(10):889–894.

Southern, E.M. (1990) "Support–bound oligonucleotides" *Chem.Abstr.* 113:835, Abstract No. 152979r.

Goldmann, T. and Gonzalez, J. S. (Mar. 2000). "DNA–Printing: Utilization of a Standard Inkjet Printer for the Transfer of Nucleic Acids to Solid Supports," *J. Biochem. Biophys. Methods* 42(3):105–110.

Lemieux, B. et al. (1998). "Overview of DNA Chip Technology," *Molecular Breeding* 4:277–289.

Lemmo, A.V. et al. (Feb. 1997). "Characterization of an Inkjet Chemical Microdispenser for Combinatorial Library Synthesis," *Analytical Chemistry* 69(4):543–551.

NASA, Lewis Research Center, (Aug. 1998). "Technology Opportunity: The Directional Electrostatic Accretion Process,"Materials & Structures MS–200–1.2 pages. http://technology.nasa.gov/scripts/nls_ax.dll/twdisp-Matches(111;20221218;1) Last visited on Sep. 4, 2002.

NASA, Glenn Research Center, (Oct. 2001). "Technology Opportunity: Acoustic Micro–Dispensing," Combustion & Fluids TOP3–00130. 2 pages. http://technology.nasa.gov/scripts/nls_ax.dll/twDispMatches(111;20221218;1) Last visited on Sep. 4, 2002.

NASA, Lewis Research Center, (Aug. 1998). "Technology Opportunity: Liquid Manipulation by Acoustic Radiation Pressure," Combustion & Fluids CF–070–1.2 pages. http://technology.nasa.gov/scripts/nls_ax.dll/twDisp-Matches(111;20221218;1) Last visited on Sep. 4, 2002.

NASA, Glenn Research Center, "Acoustically Enhanced Electroplating Process," Alchemitron Corporation, 1 page. http://technology.nasa.gov/scripts/nls_ax.dll/twDisp-Matches(22;20221218;1) Last visited on Sep. 4, 2002.

NASA, Glenn Research Center, "Acoustic Liquid Manipulation Improves Selective Plating Process," 1 page. http://technology.nasa.gov/scripts/nls_ax.dll/twDisp-Matches(22;20221218;1) Last visited on Sep. 4, 2002.

* cited by examiner

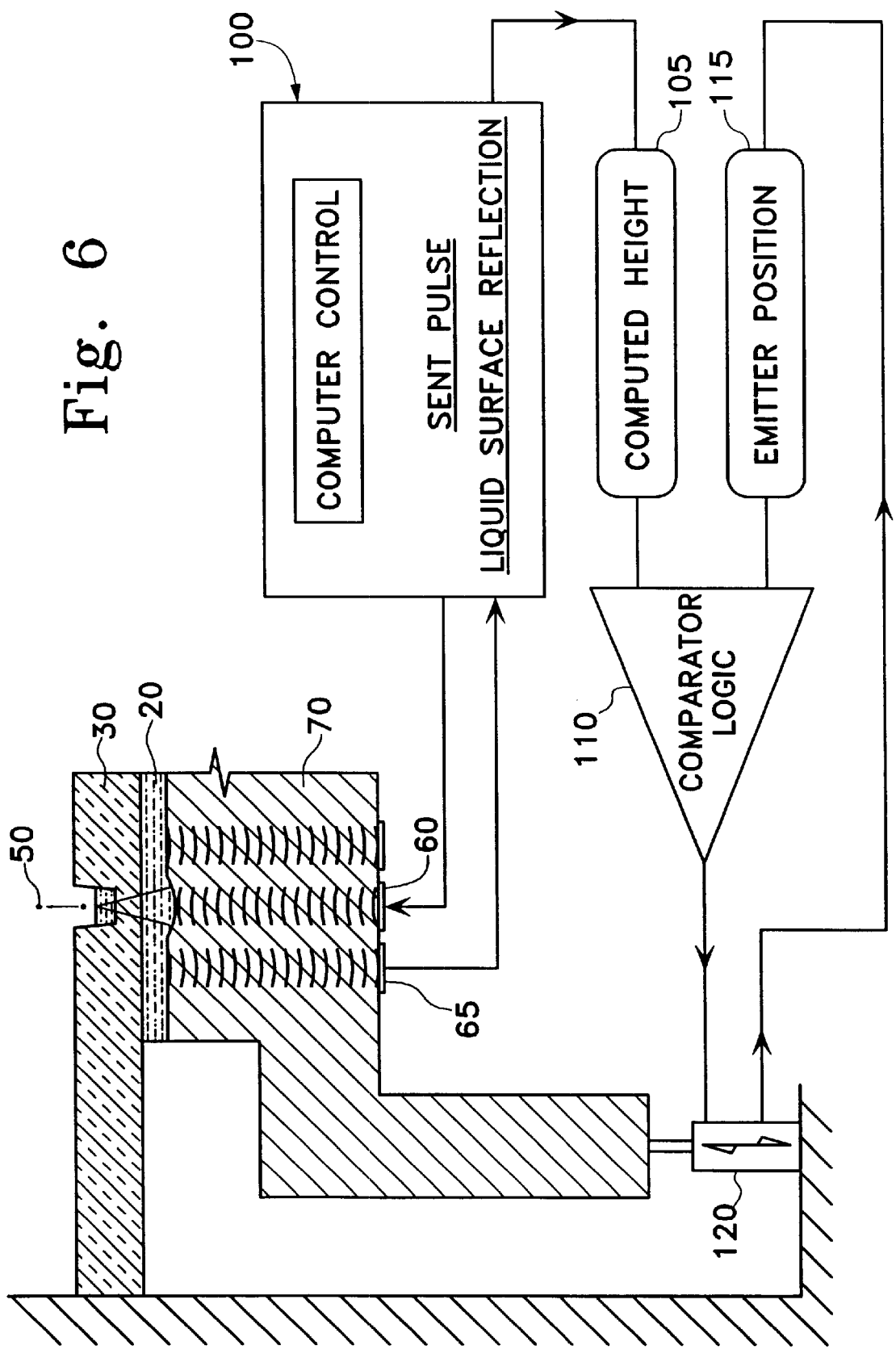

ACOUSTICALLY MEDIATED FLUID TRANSFER METHODS AND USES THEREOF

FIELD OF THE INVENTION

The present invention relates to non-contact fluid transfer methods, apparatus and uses thereof

BACKGROUND

Many methods for the precision transfer and handling of fluids are known and used in a variety of commercial and industrial applications. The presently burgeoning industries of biotechnology and biopharmaceuticals are particularly relevant examples of industries requiring ultra-pure fluid handling and transfer techniques. Not only is purity a concern, current biotechnological screening and manufacturing methods also require high throughput to efficiently conduct screening of compound libraries, synthesis of screening components, and the like.

Current fluid transfer methods require contacting the fluid with a transfer device, e.g., a pipette, a pin, or the like. Such contact methods dramatically increase the likelihood of contamination. Many biotechnology procedures, e.g., polymerase chain reaction (PCR), have a sensitivity that results in essentially a zero tolerance for contamination. Accordingly, a non-contact method for fluid transfer would result in a drastic reduction in opportunities for sample contamination.

Current biotechnology screening techniques may involve many thousands of separate screening operations, with the concomitant need for many thousands of fluid transfer operations in which small volumes of fluid are transferred from a fluid source (e.g., a multi-well plate comprising, for example, a library of test compounds) to a target (e.g., a site where a test compound is contacted with a defined set of components). Thus, not only the source, but also the target may comprise thousands of loci that need to be accessed in a rapid, contamination-free manner.

Similarly, biotechnology synthesis methods for the generation of tools useful for conducting molecular biology research often require many iterations of a procedure that must be conducted without contamination and with precision. For example, oligonucleotides of varying lengths are tools that are commonly employed in molecular biology research applications, as, for example, probes, primers, anti-sense strands, and the like. Traditional synthesis techniques comprise the stepwise addition of a single nucleotide at a time to a growing oligomer strand. Contamination of the strand with an erroneously placed nucleotide renders the oligonucleotide useless. Accordingly, a non-contact method for transferring nucleotides to the reaction site of a growing oligomer would reduce the opportunity for erroneous transfer of an unwanted nucleotide that might otherwise contaminate a pipette or other traditional contact-based transfer device.

Furthermore, existing fluid transfer methods are limited, and do not conveniently and reliably produce the high efficiency, high-density arrays. Such arrays are also useful in conducting screening, synthesis, and other techniques commonly used in biotechnology.

Accordingly, there exists a need in the art for a non-contact method for the precision transfer of small amounts of fluid in a rapid manner that is easily automated to meet industry needs.

SUMMARY OF THE INVENTION

In order to overcome the deficiencies of the prior art, the present invention provides non-contact methods for the transfer of small amounts of fluid. Methods according to the present invention employ the use of acoustic waves to generate micro-droplets of fluid. In the methods, acoustic waves are propagated through a pool of a source fluid to cause the ejection of at least one, e.g., a single micro-droplet, from the surface of the pool. The droplet is ejected towards a target with sufficient force to provide for contact of the droplet with the target.

The methods of the invention are easily automated in a manner that provides for the processing of many different sources of fluid from an array of pools of source fluid, and further provides for an array of target sites to receive the micro-droplets of source fluid as they are ejected from the pools of source fluid. In this manner thousands of individual samples of source fluid can be processed and directed to the same or two or more (e.g., a thousands or more) separate target sites for further reaction, detection, and the like. Thus, the present invention, because of its non-contact methodology, not only has greater intrinsic reliability than is provided by presently available liquid ejection on demand and continuous stream piezoelectric type pumps, but also is compatible with a wider variety of liquid compounds, including liquid compounds which have relatively high viscosity and liquid compounds which contain particulate components.

The invention provides a non-contact method for transferring small amounts of source fluid to a target, said method comprising propagating an acoustic wave from an acoustic liquid deposition emitter through a source fluid containment structure into a pool of source fluid, wherein said acoustic liquid deposition emitter is in contact with said source fluid containment structure typically through a coupling medium which is interposed between said acoustic liquid deposition emitter and a first surface of said source fluid containment structure, said pool of source fluid is on a second surface of said source fluid containment structure that is opposite or adjacent to said acoustic liquid deposition emitter, and said acoustic wave causes controlled ejection of at least one droplet of said source fluid from said pool to said target.

The invention also provides a non-contact method for transferring small amounts of a source fluid to a separate target structure, said method comprising activating a piezoelectric transducer thereby propagating an acoustic wave through a coupling medium which is interposed between said piezoelectric transducer and a first surface of a source fluid containment structure, wherein said source fluid is contained on a second surface of said source fluid containment structure that is opposite said piezoelectric transducer, and said target is positioned to receive a droplet of fluid ejected from said source fluid as a result of propagation of said acoustic wave through said source fluid.

The invention further provides a method for transferring small amounts of a source fluid from a pool selected from one of a plurality of pools of source fluid located on a first surface of a source fluid containment structure, to a separate target structure without physically contacting said source fluid, said method comprising propagating an acoustic wave through said source fluid such that a single droplet of fluid is ejected from the surface of said pool of source fluid with sufficient energy to bring said droplet into contact with said target, wherein said acoustic wave is propagated from a piezoelectric transducer, said piezoelectric transducer is in contact, opposite to, or adjacent with said source fluid containment structure via a coupling medium interposed between said piezoelectric transducer and a second surface of said source fluid containment structure, said second surface of said source fluid containment structure is opposite said pool of source fluid, and said target is opposite or adjacent to said surface of said pool of source fluid.

The invention also provides an apparatus for performing non-contact transfer of small amounts of source fluid. The apparatus includes an acoustic liquid deposition emitter and a stage wherein the stage is configured to support a source fluid containment structure supported such that the acoustic liquid deposition emitter is in operative contact with the source fluid containment structure when a coupling medium is interposed there between. The apparatus may include a number of additional elements, including, for example: an acoustic wave channel structure that is mechanically coupled to the acoustic liquid deposition emitter (e.g., a piezoelectric transducer) to provide for transmission of an acoustic wave from, e.g., the piezoelectric transducer to said coupling medium; a structure for maintaining the coupling medium in operative contact with the acoustic liquid deposition emitter; a lens for focusing said acoustic wave; controls for varying one or more of frequency, voltage, and duration of an energy source used to excite the acoustic liquid deposition emitter and thereby propagate an acoustic wave; a stage actuator for user-defined positioning of the stage relative to the acoustic liquid deposition emitter; a focussing actuator for user-defined positioning of said acoustic liquid deposition emitter relative to said stage; a computer for controlling the stage actuator and/or the focussing actuator; and a fluid level detector for detecting a level of fluid in a source fluid containment structure supported by said stage.

The invention also provides a system for performing non-contact transfer of small amounts of a source fluid. The system includes a source fluid containment structure, a movable stage configured to support the source fluid containment structure, an acoustic liquid deposition emitter in operative contact with the source fluid containment structure, a coupling medium interposed between the deposition emitter and the source fluid containment structure, and a computer in operable communication with the acoustic liquid deposition emitter for varying one or more of frequency, voltage and duration of an energy source used to excite the acoustic liquid deposition emitter and wherein the computer is in communication with the movable stage for positioning the source fluid such that operative contact with the acoustic liquid deposition emitter.

BRIEF DESCRIPTION OF THE DRAWINGS

FIG. 6 is a schematic diagram illustrating an embodiment of the present invention where a computer 100 receives signals generated by a secondary piezoelectric element 65 and computes source fluid pool 105 levels from the information received. The computer of 100 then compares 110 the computed height versus the emitter position 115 and controls the focus of the primary piezoelectric element by moving the emitter (60 of FIG. 2) relative to position the source fluid pool (40 of FIG. 2) using positioning stage 120 to most effectively eject droplet(s) from the surface of the source fluid pool (40 of FIG. 2).

DETAILED DESCRIPTION OF THE INVENTION

Figure 1:
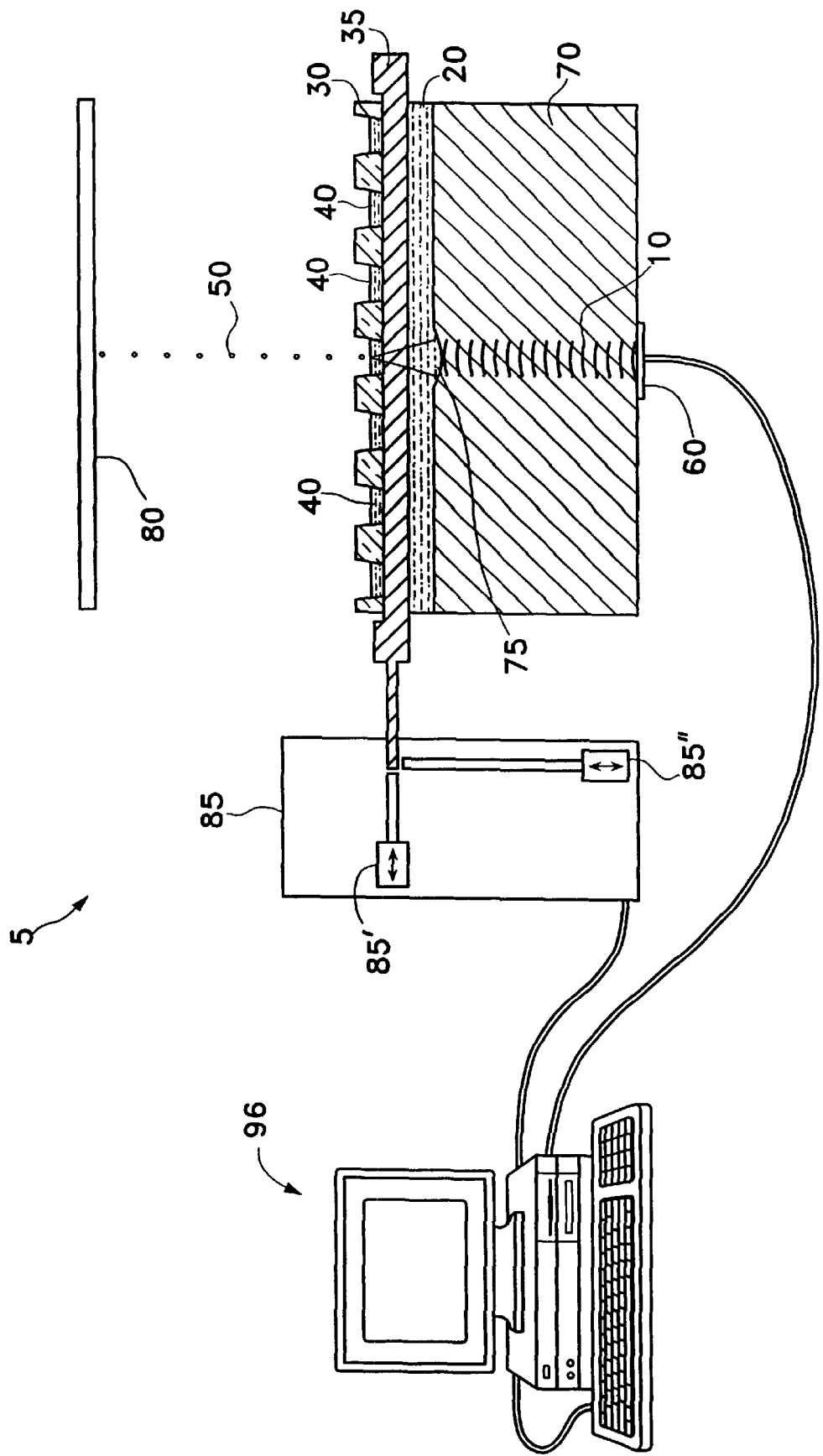
FIG. 1 is a schematic diagram illustrating one embodiment of a non-contact fluid transfer apparatus of the present invention.

In accordance with the present invention, there is provided an apparatus useful for non-contact fluid transfer. With reference to FIG. 1 there is schematically presented one embodiment of an apparatus of the present invention. The figure depicts a non-contact fluid transfer apparatus 5 having at least one acoustic liquid deposition emitter 60 in electrical communication with a computer 95. During operation the acoustic liquid deposition emitter 60 generates an acoustic wave or beam 10 that can be propagated through an optional wave channel 70. The acoustic wave can be focused by lens 75 prior to propagating through coupling fluid 20 to optimize the energy of the acoustic wave or beam 10 upon the liquid/air interface of source fluid 40. The acoustic wave 10 is propagated through a coupling medium 20 after which the wave is transmitted through source fluid containment structure 30 where the wave comes to focus at or near the surface of a pool of source fluid 40 thereby causing ejection of at least one droplet 50 of source fluid from the surface of the pool. In one embodiment, the ejected droplet 50 makes contact with a target 80. The source fluid containment structure 30 can be held on a movable stage 35. The movable stage 35 is controlled by actuator mechanism 85 which contains a horizontal actuator 85' or a vertical actuator 85" or a combination of the two actuators to control the movement of the stage 35 in both the vertical and horizontal directions. The actuator 85 is typically in communication with computer 95 which controls the movement of the stage to select a source fluid 40 or to adjust focusing of the acoustic wave or beam 10 upon the source fluid 40. The computer may have implemented thereon various algorithms to adjust the focal length and energy of the acoustic deposition emitter as well as control and manage the location of the acoustic deposition emitter relative to a particular source fluid present in or on a source fluid containment structure.

In accordance with the present invention, there are provided non-contact methods for transferring small amounts of source fluid to a target. The methods of the invention comprise propagating an acoustic wave from an acoustic liquid deposition emitter through a source fluid containment structure into a pool of source fluid. The acoustic liquid deposition emitter is coupled with the source fluid containment structure typically through a coupling medium, which is interposed between the acoustic liquid deposition emitter and a first surface of the source fluid containment structure. The pool of source fluid is on a second surface of the source fluid containment structure, and the second surface is opposite the first surface, which is in contact with the coupling medium. Thus, the acoustic wave is emitted from the acoustic liquid deposition emitter, propagates through the coupling medium, across or through the source fluid containment structure to cause controlled ejection of at least one droplet of the source fluid from the pool to the target. By "at least one droplet" means one or more droplets or a plurality of droplets. The droplets can be ejected substantially simultaneously or sequentially. In preferred embodiments a single individual droplet is ejected using the methods of the invention.

Figure 2:
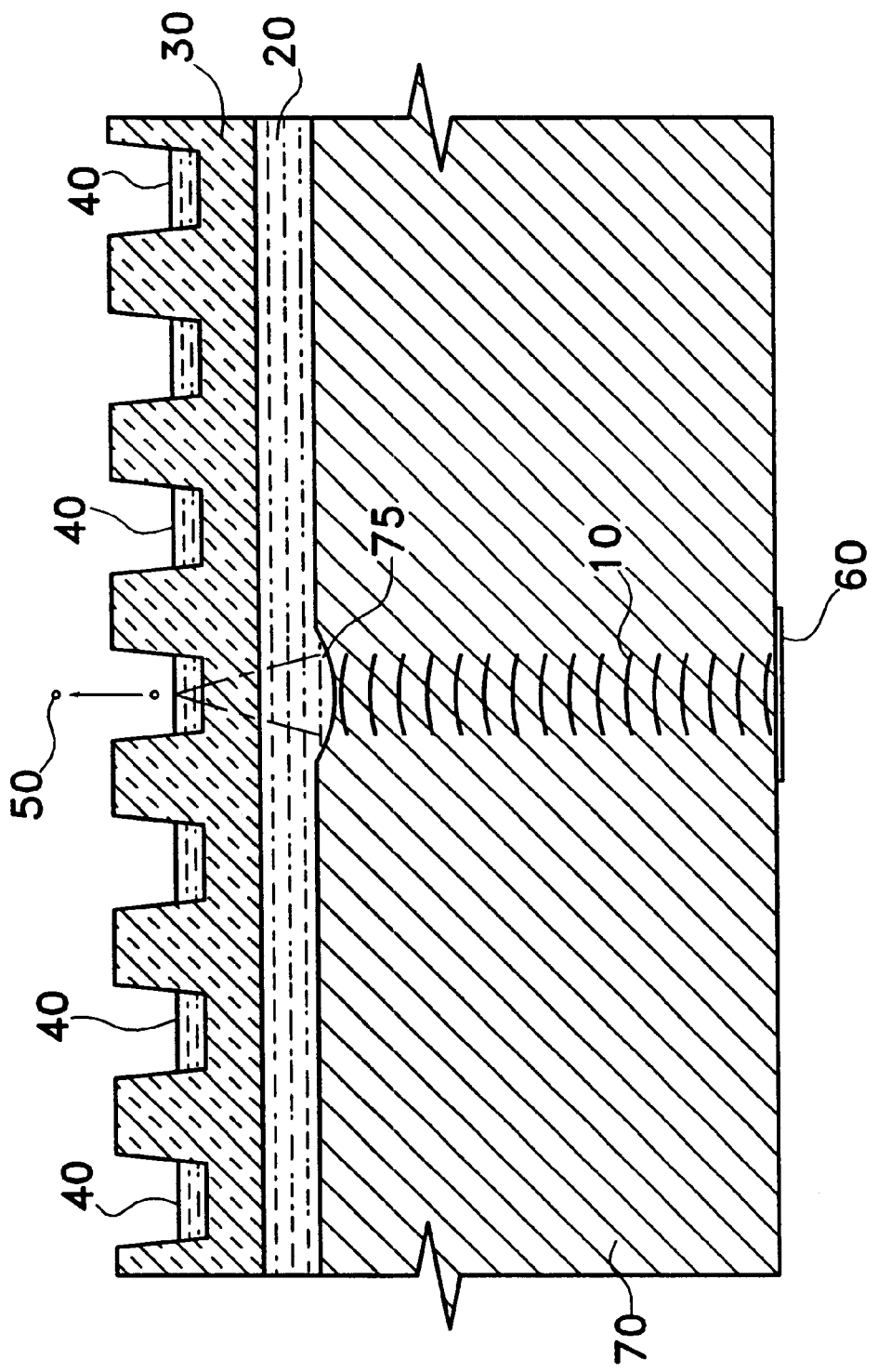
FIG. 2 is a schematic diagram illustrating one embodiment of the present invention, where an acoustic wave 10 generated by a piezoelectric element 60 is propagated through a wave channel 70, a coupling medium 20 and a source fluid containment structure 30 to a pool of source fluid 40, causing ejection of a droplet 50 of source fluid from the surface of the pool.
Figure 3:
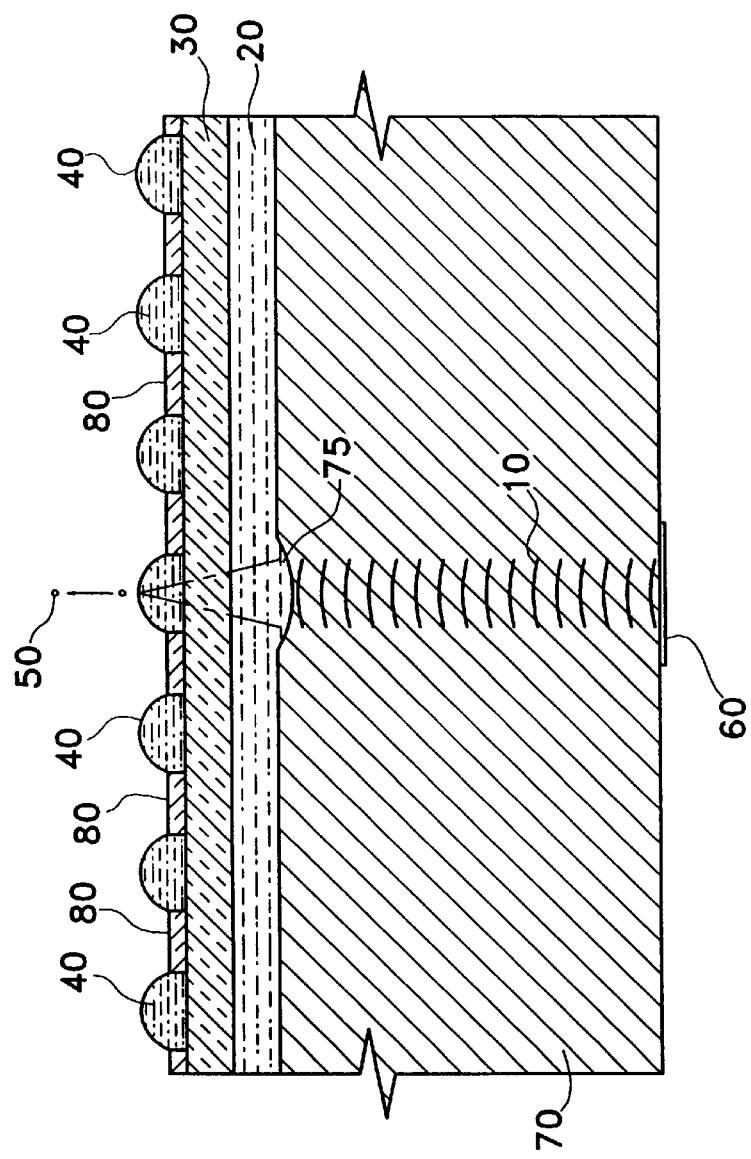
FIG. 3 is a schematic diagram illustrating an embodiment of the present invention where each pool of source fluid 40 is confined by a coating of a hydrophobic material 80 on source fluid containment structure 30.

For an example of one embodiment of the present invention, reference is made to FIG. 2 which shows the propagation of an acoustic wave 10 through a coupling medium 20 after which the wave is transmitted through source fluid containment structure 30 where the wave comes to focus at or near the surface of a pool of source fluid 40 thereby causing ejection of at least one droplet 50 of source fluid from the surface of the pool.

As used in the context of the coupling medium, "coupled with" or "coupled to" means that the coupling medium provides a medium for the acoustic waves to travel between the acoustic liquid deposition emitter and the fluid containment structure. In a preferred embodiment, the coupling medium is in contact with both the acoustic liquid deposition emitter and a first surface of the fluid containment structure (e.g., the underside of the structure, if the fluid containment structure is oriented with source fluid on its top surface).

As used herein, "controlled ejection" means that the acoustic wave can be adjusted, as further described herein, to vary the size and/or number of droplets ejected from the surface of the pool. Such controlled ejection techniques can involve adjusting or focusing of the acoustic wave, frequency of the acoustic wave, modifying the distance between the acoustic liquid deposition emitter and the source fluid, and the like, in response to the type of source fluid (e.g., the source fluids content, viscosity and the like) as well as changes in the volume or level of the source fluid during ejection of droplets or as a result of evaporation.

Accordingly, the methods of the invention rely on the fact that an acoustic wave may be propagated through a pool of fluid in a manner that causes ejection of a single droplet of fluid from the surface of the pool of fluid to assist in transferring the fluid from the source pool to a desired target. Because the acoustic wave is of sufficient energy and properly focused to eject at least one droplet of fluid from the surface of the source pool, no pipettes or other fluid handling devices need come into contact with the source pool of fluid.

Any type of fluid is suitable for use in the practice of the present invention. As used herein, "fluid" means an aggregate of matter in which the molecules are able to flow past each other without limit and without the formation of fracture planes. Thus, as recognized by those of skill in the art, a fluid may comprise a liquid and/or a gas under the appropriate conditions. A fluid may be homogenous, i.e., one component, or heterogeneous, i.e., more than one component. Where a plurality of pools of source fluid are employed in the practice of the present invention, each pool may comprise a different source fluid, as further described herein.

"Non-contact," as used herein, means that a source fluid is transferred or removed from a source pool of fluid without contacting the source fluid with a transfer device. In one embodiment, the source fluid is transferred from a source pool of fluid to a target without contacting the source fluid with a transfer device. For example, the ejection of a droplet of source fluid from the source fluid containment structure does not contact anything other than the target towards which the droplet is directed. Thus, no pipettes, pins, capillaries or other fluid transfer devices are brought into contact with the source fluid. In this manner, opportunities for contamination of the fluid and the system are minimized. Moreover, non-contact fluid transfer as described herein does not require the use of nozzles with small ejection orifices that easily clog. In addition, the relatively high cost piezoelectric transducers and acoustic focusing lenses remain as fixed components of the fluid delivery/transfer system, while the fluid(s) being transferred, as well as the fluid containment structure, may constitute separate and disposable components. This allows for a greatly improved cost of ownership because the relatively high cost piezoelectric transducer(s) and acoustic focusing lens(es) never contact the individual fluid compounds.

As used herein, "source fluid containment structure" is any structure suitable for containing or supporting a pool of source fluid and which allows an acoustic wave to propagate from a first side or end of the structure, through the structure to the second side or end of the structure, wherein the source fluid is contained on the second side or within the structure. Thus, suitable source fluid containment structures include a flat structure such as a slide (e.g., a glass or polystyrene microscope slide), or the like, onto which one or more discrete pools of source fluid may be deposited; also included are single and multi-well plates commonly used in molecular biology applications; capillaries (e.g., capillary arrays); and the like.

Maintaining discrete pools of source fluid may be accomplished by a variety of methods, including providing a plurality of separation structures such as wells, tubes or other devices that have at least one wall separating one fluid from another, or by providing coatings that serve to define containment regions (as further described herein), and the like. Immiscible fluids or materials can be used to separate dissimilar fluids (e.g., waxy coatings separating hydrophilic fluids) forming containment fields.

Source fluid containment structures may be constructed of any suitable material, bearing in mind the need for good acoustic velocity properties. Such materials include glass, polymer (e.g., polystyrene), metal, a textured material, a containment field, and the like, as well as combinations thereof. The material may further be porous or non-porous, or combinations thereof.

Source fluid containment structures may have one or more coatings to facilitate fluid containment. Thus, in one embodiment of the present invention, slides having zones of relative hydrophobicity and hydrophilicity may be employed as source fluid containment structures. In this manner, an aqueous fluid may be applied to a zone of the slide that is surrounded by a relatively hydrophobic region (or coating of relatively hydrophilic material), thereby operating to contain a pool of source fluid. Reference is made to FIG. 3 as one example of this embodiment of the present invention. Source fluid containment structure 30 has zones or regions (i.e., containment zones) for containing discrete pools of source fluid 40. These zones are defined by a coating of a hydrophobic material 80 which acts to confine the source fluid 40 in the containment zones. Accordingly, in this embodiment of the present invention, sample wells are not required to contain the discrete pools of source fluid. Examples of hydrophobic coatings include polytetratfluoroethylene (PTFE), hydrophobic amino acids, polypeptides comprising hydrophobic amino acids, waxes, oils, fatty acids, and the like. Those of skill in the art can readily determine a number of other hydrophobic coatings, which may also serve to define source fluid containment zones, and contain source fluids therein. Optionally, the zone(s) of the slide which are chosen to contain non-aqueous source fluid may have relatively hydrophilic regions (or coating of relatively hydrophilic material) to further define the containment zone(s). Thus, pools of source fluid can be confined to defined areas of a slide by virtue of the relative areas of hydrophobicity and hydrophilicity. Again, sample wells are not required to contain a pool of source fluid.

The methods of the invention are contemplated for use in high throughput operations. It is preferred that the source fluid containment structure have multiple containment regions, preferably in an array which can be mapped so that each containment region can be accessed under direction of a controlling computer. Thus, in one preferred embodiment of the present invention, the source fluid containment structure is a multi-well plate such as a micro-titer plate (comprising a plurality of wells, each having a bottom, sides and an open top for the ejection of a droplet there through). Suitable micro-titer plates may have from about 96 to about 1500 wells, or more. One example of a suitable plate is a 1536 well plate (e.g., catalog number 3950 available from Coming Corporation).

As used herein, "target" means a structure or a zone towards which a droplet of source fluid is ejected, or with which the ejected droplet makes contact. The target may be constructed of any material that is suitable for receiving the ejected fluid droplet, including, for example, a glass, a polymer, a paper, a gel, a conductive material, a metal, a porous material, a non-porous material, a textured material, or the like. The material may be further coated or textured to receive and retain the droplet of fluid. Coatings contemplated for use in the practice of the present invention include polytetrafluoroethylene (PTFE), aminomethylated or highly crosslinked polystyrene-divinyl-benzene, and the like. In some embodiments of the present invention, it may be desirable to direct a fluid droplet to a measuring device or other remotely located zone, thus, the target may not comprise a tangible object but instead comprise a collection zone defined by a containment field, a conduit, a chamber, a collector, a container, or the like. In this manner, a droplet of fluid could be directed, for example, to a conduit that leads to the reaction chamber of a mass spectrometer, or the like.

In one embodiment, the target is separate in that it is not in contact with the source fluid containment structure, but rather can be held in place at a selected distance from the source containment structure. Of course the distance must be within the effective range of the droplet generated by the acoustic liquid deposition emitter. The droplets of the size ejected from the source pool are small (e.g., at least about 1 micrometer), that in a vacuum they travel a relatively large distance (i.e., many centimeters) in opposition to the force of gravity. One of skill in the art will recognize that the distance said ejected source material can travel will depend upon the size and content of the ejected fluid and the surrounding atmospheric humidity, temperature and the like. In addition, the properties of the acoustic wave (e.g., frequency and the like) generated by the liquid deposition emitter can be varied to adjust the distance and size of the ejected source fluid droplet. The formation of a given droplet is thus dependent on, for example, the frequency of the liquid deposition emitter's (e.g., a piezoelectric transducer's) oscillation. Accordingly, a target (in still air) positioned about two (2) centimeters above the surface of the source pool can easily be impacted with a droplet ejected from the surface of the source pool. Thus, while a distance in excess of a millimeter can be employed in the practice of the present invention, it is presently preferred that the target be positioned no more than about 0.25 millimeter from the surface of the source pool; and in a another preferred embodiment, the target is no more than about five (5) millimeters from the surface of the source pool.

As used herein, "acoustic deposition emitter" means any device capable of generating a directional acoustic wave capable of causing ejection of at least one droplet of fluid from the surface of a pool of fluid. As understood by those of skill in the art, an acoustic wave or beam exerts a radiation pressure against objects upon which it impinges. Thus, when an acoustic wave or beam impinges on a free surface (e.g., fluid/air interface) of a pool of fluid from beneath, the radiation pressure which it exerts against the surface of the pool may reach a sufficiently high level to release at least one individual droplet of fluid from the pool, despite the restraining force of surface tension. In a preferred embodiment, a piezoelectric transducer is employed as an acoustic deposition emitter. In one embodiment, a piezoelectric transducer comprises a flat thin piezoelectric element, which is constructed between a pair of thin film electrode plates. As is understood by those of skill in the art, when a high frequency and appropriate magnitude voltage is applied across the thin film electrode plates of a piezoelectric transducer, RF energy will cause the piezoelectric element to be excited into a thickness mode oscillation. The resultant oscillation of the piezoelectric element generates a slightly diverging acoustic beam of acoustic waves. By directing the wave or beam onto an appropriate lens having a defined radius of curvature (e.g., a spherical lens, or the like), the acoustic beam can be brought to focus at a desired point.

The radiation pressure is greatest in the acoustic wave or beam's focal region, particularly, at the pool surface where wave reflection occurs. The pressure caused by the acoustic wave or beam acts to lift a small column of liquid which appears initially as a small mound. When enough energy is applied to overcome surface tension the mound becomes a momentary liquid fountain where each tone burst emits a single droplet. Because the focused wave or beam is diffraction limited, the droplet diameter is proportional to the wavelength. Observations with water indicate that single droplet ejection occurs at a specific power level band where uniformly sized droplets form. However above this band, as one increases power level further the droplets begin to form tails which then break off into satellite droplets. Further increases in power causes the process to transition to a continuous fountain.

At energy levels just below the threshold of normal droplet ejection, a fine mist may be emitted from the source fluid. The mist may be used in situations where it is desirable to coat a surface with fine droplet coating that is $\frac{1}{10}$ to $\frac{1}{100}$ the size of the normally produced droplets.

Fountain ejection can be achieved when the power level is well beyond the normal single droplet ejection range. Fountains appear to be continuous or nearly continuous streams of liquid that eject and break up in a random fashion and produce widely distributed sizes. This mode may be used for producing a spray like coating.

In addition, it is possible to affect the trajectory of the ejected droplet by means of electrostatics. The same principals are used in the common cathode ray tube. A simple charging plate positioned parallel to the pool surface is used. The pool acts as a opposing plate similar to a capacitor. Therefore, the pool will acquire charge that is opposite that of the charging plate. When a droplet is ejected it carries an isolated charge at point where it breaks off the pool. A small diameter hole in the charging plate permits droplet charging without impeding its path. There is an acceleration experienced by the droplet so that its final velocity will be the combination of initial ejection velocity and an electrostatic acceleration. The charge electrode voltage may be manipulated to accelerate droplets if higher velocity is desired.

Deflection is accomplished in a manner identical to the cathode ray tube. The deflection plates set up an electric field perpendicular to the droplets flight path. An acceleration perpendicular to the path results in a deflected trajectory. By manipulating the deflection voltage in two axes a sweep pattern is formed.

Accordingly, to eject individual droplets from the source fluid containment structure on demand, the RF excitation of the piezoelectric element is amplitude or frequency modulated (by means well understood to those of skill in the art), thereby causing the focused acoustic beam radiation pressure exerted against the surface of the source pool of fluid to swing above and below a predetermined droplet ejection threshold level. Thus, the RF voltage applied to the piezoelectric element may be amplitude or frequency modulated and/or energy duration modulated to control the droplet ejection process. In a preferred embodiment, the RF excitation voltage is computer controlled and may be changed to account for changes in the viscosity and surface tension of the source fluid.

In one embodiment, a computer sends an analog voltage pulse to the piezoelectric transducer by an electrical wire. The voltage pulse can be controlled, for example, by a MD-E-201 Drive Electronics manufactured by Microdrop, GmbH, Muhlenweg 143, D-22844 Norderstedt, Germany. The electronics can thus control the magnitude and duration of the analog voltage pulses, and also the frequency at which the pulses are sent to the piezoelectric transducer. Each voltage pulse causes the generation of an acoustic wave from the piezoelectric transducer, which in turn is propagated through a coupling medium and into or through the source fluid thereby impinging on the surface of the source fluid. For example, an acoustic wave (e.g., a pressure wave) propagates through the coupling medium and source fluid where one droplet of source fluid is emitted under high acceleration. The size of these droplets has been shown to be very reproducible. The high acceleration of the source fluid minimizes or eliminates problems caused by source fluid surface tension and viscosity, allowing extremely small droplets to be expelled from the surface of a pool of source fluid, e.g., as small as 5 picoliter droplets have been demonstrated.

The piezoelectric transducer may employ a flat crystal disk, or other crystal designs, e.g., square, perforated disk, and the like. In a presently preferred embodiment, the piezoelectric transducer is a flat disk. Because most electronic circuits are designed for a 50 Ω (ohm) load, it is presently preferred to employ a 50 Ω ohm transducer. While any material may be used in the piezoelectric element, in a presently preferred embodiment of the invention, a Navy Type I piezoelectric material is employed in a disk element having diameter D=0.039 inch or D=0.991 mm. Other shapes of piezoelectric crystals are also contemplated for use in the practice of the present invention.

Firing of the acoustic deposition emitter may be conducted manually or under direction of a controlling computer. Because the present invention is useful in high throughput operations, it is presently preferred that firing of the acoustic deposition emitter be computer controlled. Firing of the emitter can be coordinated with computer controlled positioning of both the source containment structure or the target so that a specific source fluid can be directed to a specifically selected target spot on the target.

Proper focus of the acoustic wave can be achieved by providing a lens between the piezoelectric transducer and the coupling medium. Lenses contemplated for use in the practice of the present invention may be of constant curvature or aspherical. An aspherical lens (i.e., a lens having a compound curvature) may be employed to accommodate any irregularities in the acoustic wave, whether due to the piezoelectric element itself, a misalignment of the piezoelectric element with the surface of the pool of source fluid, or the like.

Figure 4:
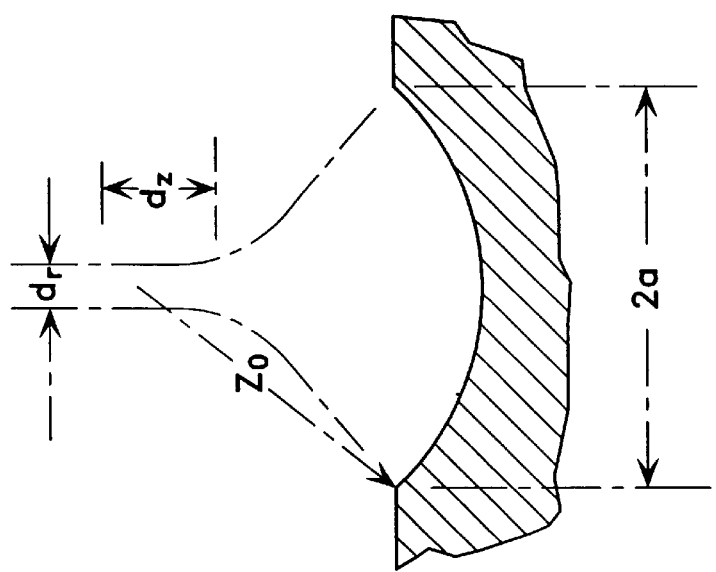
FIG. 4 depicts a lens contemplated for use in the practice of the present invention, and shows various parameters that may be adjusted to provide correct focus of an acoustic wave. The diameter of the aperture is $2a$, $Z_0$ is the focal length, $d_z$ is the depth of field, and $d_r$ is the deposition feature diameter.

To capture the maximum amount of energy emitted by the crystal, it is preferred that the lens aperture be greater than the crystal diameter. With reference to FIG. 4, the lens can be constructed with a spherical cutter, for example, to have a selected focal distance $Z_O$. It is preferred that $Z_o$=0.125 inch or 3.175 mm. This yields an f-value (f=$Z_o$/D) equal to four (4), where D is the diameter of the active area of the piezoelectric material. It is preferred that the radius of curvature of the lens be chosen to provide an f-value in the range of about 1 to 4. In another aspect of this embodiment, the f-value is in the range of 1–2. In yet another aspect of this embodiment, the f-value is in the range of 2–4.

To efficiently capture the energy in the acoustic wave generated by the piezoelectric crystal, it is desirable that the diameter of the lens be greater than the diameter of the active portion of the piezoelectric crystal. Thus, in view of the preferred active crystal diameter of 0.039 inches or 0.99 mm, the presently preferred value for the radius of the lens (a) is about 0.016 inch or 0.40 mm (see FIG. 4). In a typical embodiment, the focal distance of the lens may be approximately equal to 2.5 to 3 times the diameter of the crystal.

By virtue of having an f-value in the range of 1–4, a relatively long focal length ($d_z$) results. Consequently, the acoustic deposition emitter is functional over a wide range of depths of source pool. In this manner, refocusing of the emitter is not required every time the depth of a particular sample pool is altered by the ejection of some material therefrom. Nonetheless, in an alternative embodiment of the present invention, adjusting the focus of the acoustic beam is contemplated. Such adjustment may be made by varying the distance between the acoustic deposition emitter and the surface of the pool of source fluid. Any methods useful for varying the distance between the acoustic deposition emitter and the surface of the pool of source fluid are contemplated for use in the practice of the present invention. Focussing may be automated and controlled by computer.

By applying a particular wavelength ($\lambda$) of the acoustic wave in the source fluid, the depth of focus can be estimated by applying the formula $d_z=4.88 \cdot \lambda \cdot f^2$. The wavelength ($\lambda$) of the acoustic wave can be determined by those of skill in the art based on the velocity of sound through the chosen source fluid and the frequency of the acoustic wave. Thus, when the source fluid comprises water, the relevant equations are $$V_{H2O} = 1496 \text{ m/s}, \quad \text{and} \quad \lambda = \frac{VH2O}{\text{frequency}}$$

Droplet diameter ($d_r$) at a given $\lambda$ and f-value can be determined by applying the equation $d_r=1.02 \cdot \lambda \cdot f$. Similarly, a selected droplet diameter can be achieved by solving the preceding equation for $\lambda$, and employing acoustic waves of that wavelength.

By applying the forgoing equations to the preferred values for variables (f) and (a) disclosed herein, and assuming a source fluid comprising water, the wavelength $\lambda=75$ $\mu$m; the focal length $d_z=3.75$ mm; and the droplet diameter $d_r=245$ $\mu$m.

The size of the droplet can also be adjusted by modulating one or more of frequency, voltage, and duration of the energy source used to excite the acoustic liquid deposition emitter (e.g., a piezoelectric transducer). Accordingly, a wide range of user-defined droplet diameters can be achieved by employing the methods of the invention. In one embodiment of the present invention, the defined droplet diameter is at least about 1 micrometer. In another embodiment of the present invention, the defined droplet diameter is in the range of about 1 micrometer to about 10,000 micrometers. In yet another embodiment of the present invention, the defined droplet diameter is in the range of about 500 micrometers to about 1000 micrometers. In a further embodiment of the present invention, the defined droplet diameter is in the range of about 60 micrometers to about 500 micrometers. In yet another embodiment of the present invention, the defined droplet diameter is in the range of about 100 micrometers to about 500 micrometers. In another embodiment of the present invention, the defined droplet diameter is in the range of about 120 micrometers to about 250 micrometers. In a further embodiment of the present invention, the defined droplet diameter is in the range of about 30 micrometers to about 60 micrometers. In still another embodiment of the present invention, the defined droplet diameter is about 50 micrometers.

It is preferred that acoustic waves be channeled from the liquid deposition emitter (e.g., piezoelectric element) to the source fluid via an acoustic wave channel. Reference is made to FIG. 2 which shows an acoustic wave 10 being generated by a piezoelectric element 60 and propagated through acoustic wave channel 70. The rapid oscillation of the piezoelectric element 60 generates an acoustic wave 10, which propagates through the acoustic wave channel 70 at a relatively high velocity until it strikes the focusing lens 75. The wave then emerges into a medium 20 (i.e., the coupling medium) having a much lower acoustic velocity, so the spherical shape of the lens imparts a spherical wave-front to it, thereby forming the acoustic beam. The acoustic wave channel 70 may be constructed of aluminum, silicon, silicon nitride, silicon carbide, sapphire, fused quartz, certain glasses, or the like. In a preferred embodiment, the acoustic wave channel 70 is constructed of aluminum. Each of the aforementioned materials is chosen because of its high acoustic velocity type properties. In general, suitable materials have an acoustic velocity, which is higher than the acoustic velocity of the source fluid. It is also preferred that the piezoelectric element 60 is deposited on or otherwise intimately mechanically coupled to a surface of the acoustic wave channel 70.

In a preferred embodiment, a sufficiently high refractive index ratio is maintained between the acoustic wave channel and the source containment structure by providing a temperature controlled liquid transition interface (e.g., a temperature controlled coupling medium as described herein) that couples the highly focused acoustic wave or beam with a containment structure. The focusing lens should direct the beam into an essentially diffraction limited focus at or near the fluid/air interface at the surface of the source fluid pool.

As used herein "coupling medium" means a fluid medium having an acoustic impedance that is substantially the same as the acoustic impedance of the source fluid containment structure. The coupling medium will be in contact with both an acoustic liquid deposition emitter or preferably the acoustic wave channel and one side of the fluid containment structure, thereby providing for efficient energy transfer from the acoustic wave channel to the fluid containment structure, and subsequently through the source fluid. As an example, a polystyrene multi-well plate has an acoustic impedance of about 2.3. Water has an acoustic impedance of about 1.7. Accordingly, water is a good coupling medium when the source fluid containment structure is a polystyrene device (e.g., a multi-well plate) due the close match in impedence values between water and the plate. By adding other fluids (e.g., glycerol, or the like) to the water, an even closer match can be achieved. Other fluids may also be employed in the practice of the present invention.

Thus, by providing a coupling medium between the acoustic wave deposition emitter or preferably the acoustic wave channel and the fluid containment structure, a far more efficient transfer of energy occurs than if no coupling medium is employed. In one aspect of the invention, the coupling medium is temperature controlled to minimize any effect of temperature on the source fluid.

Because these methods may be employed in high throughput applications, it is preferred that methods of the invention further comprise user-defined positioning of the acoustic liquid deposition emitter relative to an array of source wells, thus providing for user-defined association of the acoustic liquid deposition emitter with a selected pool of source fluid for ejection of a droplet therefrom. This can be accomplished by a variety of methods. For example, in the case where a multi-well plate is employed as the source fluid containment structure, a computer-controlled translator (e.g., an actuator, or the like) can manipulate the position of the multi-well plate or a movable stage upon which the multiwell plate rests. Thus, a selected well or a selected succession of wells is placed over the acoustic deposition emitter, as the source fluid contained in each well is needed for the application being conducted (e.g., oligonucleotide synthesis, or the like). In a related embodiment, the acoustic deposition emitter may be moved rather than the source plate. For example, the source fluid containment structure may remain fixed in position and the acoustic liquid deposition emitter may be moved relative to a well or particular source fluid of interest contained in or on the source fluid containment structure. In yet another embodiment, multiple deposition emitters may be utilized each associated, for example, with a source fluid pool. In this embodiment, neither the source fluid containment structure nor the deposition emitter are moved but rather the deposition emitters are selectively activated depending upon which source fluid is desired to have at least one droplet ejected there from. Once again, this allows for the selective association of the emitter with a selected source pool. Accordingly, a source fluid array having a plurality of different source fluid materials may have droplets selectively ejected from a particular source fluid towards, for example, a target.

The target may comprise an array of target zones or target spots to which source fluid is directed. As described above, with respect to the source fluid and acoustic deposition emitter, the target may also be moveable relative to a source fluid. For example, the target may be moved relative to a source fluid to be ejected thereby allowing for selected receipt at the target of a desired ejected source fluid droplet. The target may be positioned so that each target zone can be selectively positioned over the selected pool of source fluid. A computer controlled actuator arm, or the like can accomplish positioning of the target. It is presently preferred that both the target and the source fluid containment structure be positionable via separate computer-controlled actuators. Thus, the non-contact fluid transfer/deposition technology described herein provides for precise targeting of individual source fluids to selected target zones.

Source fluids contemplated for use in the practice of the present invention may comprise one or more source materials. Source materials may include both biological and chemical compounds, agents and life forms (e.g., plant cells, eukaryotic or prokaryotic cells).

As used herein, "biological compounds" may comprise nucleic acids (e.g., polynucleotides), peptides and polypeptides (including antibodies and fragments of antibodies), carbohydrates (e.g., oligosaccharides), and combinations thereof. In some embodiments, cells (e.g., eukaryotic or prokaryotic) may be contained in the fluid. Such an embodiment would allow for the transfer of organisms from one source fluid to another fluid or target during cell culturing or sorting.

The term "polynucleotides" and "oligonucleotides" include two or more nucleotide bases (e.g., deoxyribonucleic acids or ribonucleic acids) linked by a phosphodiester bond. Accordingly, such polynucleotides and oligonucleotides include DNA, cDNA and RNA sequences. Polynucleotides and oligonucleotides may comprise nucleotide analogs, substituted nucleotides, and the like. Nucleic acids contemplated for use in the practice of the present invention include naked DNA, naked RNA, naked plasmid DNA, either supercoiled or linear, and encapsulated DNA or RNA (e.g., in liposomes, microspheres, or the like). As will be understood by those of skill in the art, particles mixed with plasmid so as to "condense" the DNA molecule may also be employed.

Polypeptides contemplated for use in the practice of the present invention includes two or more amino acids joined to one another by peptide bonds. Thus, polypeptides include proteins (e.g., enzymes (e.g., DNA polymerase), structural proteins (e.g., keratin), antibodies, fragments thereof, and the like), prions, and the like.

"Chemical compounds" contemplated for use in the practice of the present invention may comprise any compound that does not fall under the definition of biological compounds as used herein. Specific chemical compounds contemplated for use in the practice of the present invention includes dyes, detectable labels, non-enzyme chemical reagents, dilutents, and the like.

As used herein, the terms "detectable label", "indicating group", "indicating label" and grammatical variations thereof, refer to single atoms and molecules that are either directly or indirectly involved in the production of a detectable signal. Any label or indicating agent can be linked to or incorporated in a nucleic acid, a polypeptide, polypeptide fragment, antibody molecule or fragment thereof, and the like. These atoms or molecules can be used alone or in conjunction with additional reagents. Such labels are themselves well known in the art.

The detectable label can be a fluorescent-labeling agent that chemically binds to proteins without denaturation to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-1-naphthalenesulfonyl chloride (DANSC), tetramethyl-rhodamine isothiocyanate (TRITC), lissamine, rhodamine 8200 sulphonyl chloride (RB-200-SC), and the like. A description of immunofluorescence analytic techniques is found in DeLuca, "Immunofluorescence Analysis", in Antibody as a Tool, Marchalonis et al., eds., John Wiley & Sons, Ltd., pp. 189–231 (1982), which is incorporated herein by reference.

The detectable label may be an enzyme, such as horseradish peroxidase (HRP), glucose oxidase, and the like. In such cases where the principal indicating label is an enzyme, additional reagents are required for the production of a visible signal. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

In another embodiment, radioactive elements are employed as labeling agents. An exemplary radiolabeling agent is a radioactive element that produces gamma ray emissions, positron emissions, or beta emissions. Elements that emit gamma rays, such as $^{124}I$, $^{125}I$, $^{126}I$, $^{131}I$ and $^{51}Cr$, represent one class of radioactive element indicating groups. Beta emitters include $^{32}P$, $^{111}Indium$, $^{3}H$, and the like.

The linking of a label to a substrate (e.g., labeling of nucleic acids, antibodies, polypeptides, proteins, and the like), is well known in the art. For instance, antibody molecules can be labeled by metabolic incorporation of radiolabeled amino acids provided in the culture medium. See, for example, Galtre et al., Methods of Enzymology, 73:3–46 (1981). Conventional means of protein conjugation or coupling by activated functional groups are particularly applicable. See, for example, Aurameas et al., Scandinavia Journal of Immunology. Vol. 8, Suppl. 7:7–23 (1978), Rodwell et al., Biotech., 3:889–894 (1984), and U.S. Pat. No. 4,493,795.

In one embodiment, the methods of the present invention may be used to pair certain ligands (i.e., a molecular group that binds to another entity to form a larger more complex entity) and binding partners for such ligands. For example, certain biological molecules are known to interact and bind to other molecules in a very specific manner. Essentially any molecules having a high binding specificity or affinity for each other can be considered a ligand/binding partner pair, e.g., a vitamin binding to a protein, a hormone binding to a cell-surface receptor, a drug binding to a cell-surface receptor, a glycoprotein serving to identify a particular cell to its neighbors, an antibody (e.g., IgG-class) binding to an antigenic determinant, an oligonucleotide sequence binding to its complementary fragment of RNA or DNA, and the like.

Such pairings are useful in screening techniques, synthesis techniques, and the like. Accordingly, in one embodiment of the present invention, screening assays may be performed in which the binding specificity of one compound for another is sought to be determined. For example, multiple test compounds (i.e., putative ligands, optionally having detectable labels attached) may be screened for specific interaction with a selected binding partner. Such assays may be carried out by positioning one of a plurality of putative ligands in each pool of an array of source fluids. The target may comprise, for example, an array of target zones, each zone having affixed to it a sample of the binding partner for which specific binding is sought to be identified. Employing the methods of the invention, a droplet of each putative ligand can be ejected to a target zone and the target thereafter washed under defined conditions. Afterwards, each of the target zones is inspected to determine whether binding of the putative ligand has occurred. Binding of a putative ligand serves to identify that compound as a ligand for the binding partner. Binding can easily be identified by any method known to those of skill in the art. By employing detectable labeled test compounds, binding can readily be determined by identifying a labeled compound bound to the target. Of course, such assays may be reversed, i.e., the selected binding partner may be used as a labeled source compound, while putative ligands are arrayed onto the target.

In one aspect of the foregoing embodiment, the methods of the invention may also be applied to the identification of peptides or peptide mimetics that bind biologically important receptors. In this aspect, a plurality of peptides of known sequence can be applied to a target to form an array using methods described herein. The resulting array of peptides can then be used in binding assays with selected receptors (or other binding partners) to screen for peptide mimetics of receptor agonists and antagonists. Thus, the invention provides a method for producing peptide arrays on a target, and methods of using such peptide arrays to screen for peptide mimetics of receptor agonists and antagonists.

The specific binding properties of binding partners to ligands have implications for many fields. For example, the strong binding affinity of antibodies for specific antigenic determinants is critical to the field of immunodiagnostics. Additionally, pharmaceutical drug discovery, in many cases, involves discovering novel drugs having desirable patterns of specificity for naturally occurring receptors or other biologically important binding partners. Many other areas of research exist in which the selective interaction of binding partners for ligands is important and are readily apparent to those skilled in the art.

The methods of the invention may also be employed in synthesis reactions. For example, in another embodiment of the present invention, employing monomeric and/or multimeric nucleotides as source compounds can be employed to synthesize oligonucleotides (useful as probes, labels, primers, anti-sense molecules, and the like). Such source compounds may be present in a fluid medium (i.e., source fluid) and each source fluid placed in a defined position of an array on the source containment structure. By ejecting source nucleotides from the source containment structure onto a defined target zone of the target, defined nucleotides can be added to a growing product oligonucleotide chain in an additive manner that serves to define the nucleotide sequence of the growing product oligonucleotide.

The particular chemical reactions necessary to perform oligonucleotide synthesis are well known to those of skill in the art. Such reactions, or others, which may become known, can be performed in situ on the target by, for example, contacting the growing oligonucleotide with the necessary reagents between each iterative addition of further nucleotide(s). Flowing the reagents across the target, by passing the target through a reagent bath, or the like can perform reagent contacting. By employing a target with a suitable coating or having suitable surface properties, the growing oligonucleotide can be bound to the target with sufficient strength to undergo the necessary chemical reactions, after which the mature oligonucleotide can be released from the target. For example, methods for attaching oligonucleotides to glass plates in a manner suitable for oligonucleotide synthesis are known in the art. Southern, Chem. abst. 113; 152979r (1990), incorporated by reference herein in its entirety, describes a stable phosphate ester linkage for permanent attachment of oligonucleotides to a glass surface. Mandenius et al., Anal. Biochem. 157; 283 (1986), incorporated by reference herein in its entirety, teaches that the hydroxyalkyl group resembles the 5'-hydroxyl of oligonucleotides and provides a stable anchor on which to initiate solid phase synthesis. Other such binding/release technologies are also known or may become available and are thus contemplated for use in the practice of the present invention.

The efficiency of oligonucleotide synthesis can be greatly enhanced by employing nucleotide building blocks that are a combination of monomers and multimers. Examples of nucleotide building blocks include nucleotides, analogues or derivatives thereof containing reactive, blocking or other groups rendering the nucleotide building block suitable for reaction to form oligonucleotides. Thus, in a particular aspect of the forgoing synthesis embodiment, there are provided methods for oligonucleotide synthesis in which each source pool contains an aliquot comprising one member from the group consisting of an oligonucleotide of 10 or more nucleic acid bases, a dimeric oligonucleotide (e.g., all possible combinations of an oligonucleotide comprising two nucleotide bases), a trimeric oligonucleotide (e.g., all possible combinations of an oligonucleotide comprising three nucleotide bases), a tetrameric oligonucleotide (e.g., all possible combinations of an oligonucleotide comprising four nucleotide bases), and a pentameric oligonucleotide (e.g., all possible combinations of an oligonucleotide comprising five nucleotide bases). As used herein a nucleotide base is selected from the group consisting of adenine, cytosine, guanine and thymine (or uracil). A complete set of all possible nucleotide combinations equals 1,024 possible pentamers combinations, 256 tetramers combinations, 64 trimers combinations, 16 dimers combinations, and 4 monomers, which can easily be placed into an industry standard 1,536 well plate, as only 1,364 individual wells are required of the total 1,536 available. A computer can determine the most efficient synthesis scheme for a desired product oligonucleotide by optimally selecting building blocks from the source fluid wells containing the oligonucleotide material comprising the monomer through pentamer oligonucleotides, and thereby minimize the number of steps required to synthesize the desired product oligonucleotide. For example, the present invention allows for the synthesis of $1.0995 \times 10^{12}$ possible 20-mer oligonucleotide combinations with only 4 couplings using any combination of the pentamer source fluid materials. Similarly, 12 couplings of any combination of the pentamer source fluid materials will give rise to $1.329 \times 10^{36}$ possible 60-mer oligonucleotide combinations. Thus, oligonucleotide synthesis can be automated and conducted with greater efficiency than if the synthesis were conducted by the stepwise addition of single nucleotides only. Other extended sequence iterative synthesis reactions may also be performed by the methods of the invention.

In a further embodiment of the present invention, there are provided methods for determining or confirming the nucleotide sequence of an "unknown" polynucleotide. The polynucleotide may be labeled by conventional methods (e.g., fluorescent, magnetic or nuclear) and then contacted with target oligonucleotides of known sequence that have previously been bound to an array of sites on the target using the methods of the invention (i.e., ejection of the known oligonucleotide from a source pool to a desired target zone on the target array). Indeed, the target oligonucleotides may be synthesized in situ on the target array using methods described herein. Following contacting of the "unknown" polynucleotide with the target array of oligonucleotides, the target array is washed at the appropriate stringency and the presence and location of hybridized-labeled polynucleotide is determined using scanning analyzers or the like. Since the sequence of the target oligonucleotide at each position of the target array is known, this embodiment of the invention provides for the unambiguous determination of the nucleotide sequence of the selected polynucleotide.

In performing the methods of the invention, the volume of each of the source pools is depleted as material is ejected from them. Thus, it is desirable to monitor the volume or level of each source pool to ensure fluid is available. The volume of level of source fluid is also important because the impinging acoustic wave or beam will eject droplets from the surface of the source pool most efficiently if the beam is focused as nearly as possible on the surface of the pool. Thus, by monitoring the volume or level of the source pool, the focus of the acoustic wave or beam can be adjusted (e.g., by adjusting the distance between the acoustic deposition emitter the source fluid containment structure).

Accordingly, in a further embodiment the invention provides a method for detecting the amount of source fluid remaining in a source pool. Fluid volume or level detection may be performed by a variety of methods including direct visual/optical inspection, indirect measurement, and the like. In one aspect of this embodiment, detecting is performed by optically observing a change in the source fluid volume or level as a result of ejecting said droplet from said pool. In this aspect, optical observation may be performed by an optical detector coupled to a computer, wherein the computer computes a change in volume or level based on signals received from the optical detector before ejection of a droplet, and after the ejection of a droplet.

Optical detectors contemplated for use in the practice of the present invention may include a camera, a photoelectric cell, and the like. For example, a laser or other light source can be directed at the surface of a source pool and the detraction angle determined by one or more photoelectric cells coupled to a computer. The angle can thus indicate the level of fluid in the source pool, and from there, the volume can readily be computed. Other optical detection methods known to those of skill in the art or developed in the future may also be employed in this aspect of the present invention.

Figure 5:
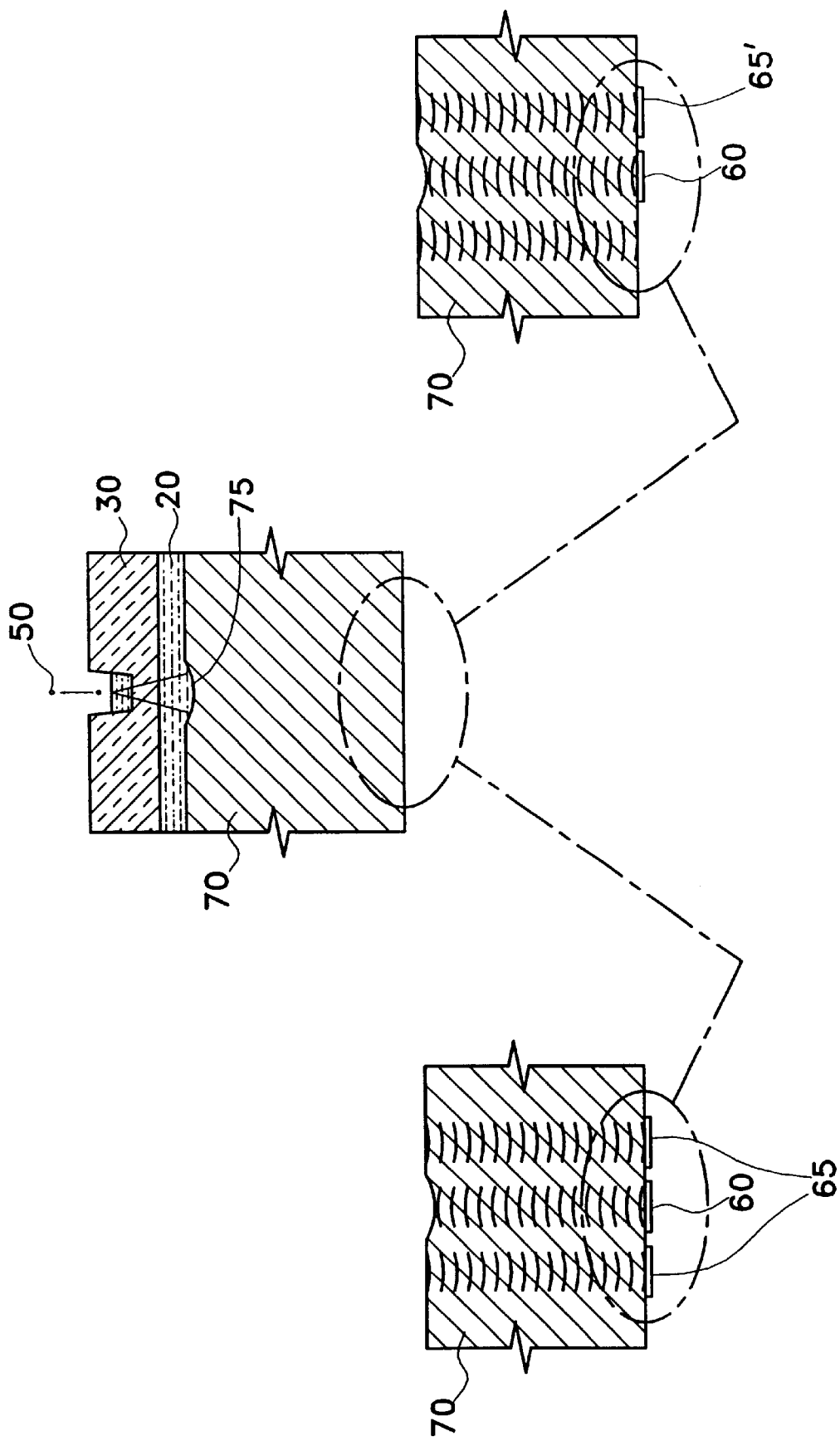
FIG. 5 is a schematic diagram illustrating several options for monitoring source fluid pool levels by monitoring acoustic waves generated by secondary piezoelectric elements 65 directed at the source fluid pool.

In another aspect of the invention, detection of the fluid level (volume and/or height) may be by observing the acoustic reflection properties of the pool of source fluid. For example, by detecting the reflection of the acoustic beam employed to eject the droplet from the surface, the volume can be computed based on empirically determined acoustic reflection characteristics. Since the acoustic liquid deposition emitter (e.g., a piezoelectric transducer) design is similar with acoustic measuring devices the droplet generator's transducer may also be used for acoustic depth sensing as a means of pool level or volume feedback measurement. The signal can be processed and the system can then be adjusted to further focus the acoustic wave or beam as the level or volume changes. In another aspect of this embodiment, a secondary piezoelectric transducer can be employed to generate the acoustic beam employed to detect the fluid level. The secondary piezoelectric transducer may be torroidal and disposed around the perimeter of the piezoelectric transducer used to eject the droplet of fluid (i.e., the primary transducer). One example of this embodiment is depicted in FIG. 5, which shows two options for deploying a secondary piezoelectric transducer. For example, a torroidal secondary transducer 65 may be disposed around the perimeter of the primary piezoelectric transducer 60. In another aspect, a non-torroidal secondary transducer 65' may be employed to generate the acoustic wave used to gauge fluid level. Other deployments of the second piezoelectric transducer may also be employed in the practice of the present invention.

Any of the forgoing embodiments for detecting fluid level may be employed in conjunction with a computer that retains and/or manipulates the values of the fluid level. In one embodiment of the present invention, an example of which is shown in FIG. 6, the liquid surface reflection of the signal from the secondary piezoelectric element is received by a computer 100 which computes the fluid level and sends a fluid level value 105 through a comparator algorithm 110 which may then be used to send a signal to an actuator 120 that operates to modulate one or more parameters (e.g., energy used to fire the piezoelectric element, distance of the piezoelectric element and/or lens from the surface of the source pool, and the like) in order to achieve the desired focus and energy of the acoustic wave. If desired, a return signal 115 of one or more values such as emitter position or the like, can be returned to the comparator algorithm for further evaluation.

In addition, a computer can be used to control any number of controllable parameters including, for example, a stage location relative to the deposition emitter (e.g., piezoelectric transducer), frequency, voltage and duration of an energy source used to excite the acoustic liquid deposition emitter.

The various techniques, methods, and aspects of the invention described above can be implemented in part or in whole using computer-based systems and methods. Additionally, computer-based systems and methods can be used to augment or enhance the functionality described above, increase the speed at which the functions can be performed, and provide additional features and aspects as a part of or in addition to those of the invention described elsewhere in this document. Various computer-based systems, methods and implementations in accordance with the above-described technology are presented below.

A computer useful in the invention can be a processor-based system including a main memory, preferably random access memory (RAM), and can also include a secondary memory. The secondary memory can include, for example, a hard disk drive and/or a removable storage drive, representing a floppy disk drive, a magnetic tape drive, an optical disk drive, etc. The removable storage drive reads from and/or writes to a removable storage medium. Removable storage media represents a floppy disk magnetic tape, optical disk, etc., which is read by and written to by removable storage drive. As will be appreciated, the removable storage media includes a computer usable storage medium having stored therein computer software and/or data. The stored data and/or software can include instructions to cause the computer to control a movable stage, frequency, voltage and duration of an energy source used to excite the acoustic liquid deposition emitter, for example.

In alternative embodiments, secondary memory may include other similar means for allowing computer programs or other instructions to be loaded into a computer system. Such means can include, for example, a removable storage unit and an interface. Examples of such can include a program cartridge and cartridge interface (such as the found in video game devices), a movable memory chip (such as an EPROM, or PROM) and associated socket, and other removable storage units and interfaces which allow software and data to be transferred from the removable storage unit to the computer system.

The computer system can also include a communications interface. Communications interfaces allow software and data to be transferred between computer system and external devices. Examples of communications interfaces can include a modem, a network interface (such as, for example, an Ethernet card), a communications port, a PCMCIA slot and card, etc. Software and data transferred via a communications interface are in the form of signals which can be electronic, electromagnetic, optical or other signals capable of being received by a communications interface. These signals are provided to the communications interface via a channel capable of carrying signals and can be implemented using a wireless medium, wire or cable, fiber optics or other communications medium. Some examples of a channel can include a phone line, a cellular phone link, a RF link, a network interface, and other communications channels. The computer interface or communications ports can be used to receive instructions or to cause an apparatus operably connected to the computer to perform a particular function.

Without further elaboration, it is believed that one skilled in the art can, using the preceding description, utilize the present invention to its fullest extent. The following examples are intended to illustrate but not to limit the invention in any manner, shape, or form, either explicitly or implicitly. While they are typical of those that might be used, other procedures, methodologies, or techniques known to those skilled in the art may alternatively be used.

While the invention has been described in detail with reference to certain preferred embodiments thereof, it will be understood that modifications and variations are within the spirit and scope of that which is described and claimed.

That which is claimed:

1. An apparatus for performing non-contact transfer of small amounts of source fluid, said apparatus comprising:
    a source fluid containment structure;
    an acoustic liquid deposition emitter separated from the source fluid containment structure by a gap, said acoustic liquid deposition emitter being positioned to direct an acoustic wave through the gap towards the source fluid containment structure; and
    a movable stage supporting the source fluid containment structure and adapted to move the source fluid containment structure relative to the acoustic liquid deposition emitter such that said acoustic liquid deposition emitter is in operative contact with said source fluid containment structure when a coupling liquid is interposed in the gap there between.

2. An apparatus for performing non-contact transfer of small amounts of source fluid to a target, said apparatus comprising (a) an acoustic liquid deposition emitter and (b) a movable stage supporting a removable source fluid containment structure and is adapted to position the source fluid containment structure relative to the acoustic liquid deposition emitter whereby the acoustic liquid deposition emitter is coupled to a first surface of the source fluid containment structure by a coupling liquid interposed between said acoustic liquid deposition emitter and said first surface of the source fluid containment structure, such that an acoustic wave generated by said acoustic liquid deposition emitter is transmitted through said coupling liquid to said first surface of the source fluid containment structure and thereafter propagates through said source fluid containment structure into a pool of source fluid on a second surface of said source fluid containment structure opposite said first surface of the source fluid containment structure, causing controlled ejection of at least one droplet of said source fluid from said pool.

3. An apparatus according to claim 1 or claim 2, wherein said acoustic liquid deposition emitter further comprises an acoustic wave channel structure.

4. An apparatus according to claim 1 or claim 2, wherein said acoustic liquid deposition emitter further comprises a lens for focusing an acoustic wave.

5. An apparatus according to claim 4, wherein said lens is spherical.

6. An apparatus according to claim 4, wherein said lens has an f value in the range of about 1 to about 4.

7. An apparatus according to claim 1 or claim 2, wherein said acoustic liquid deposition emitter comprises a piezoelectric transducer.

8. An apparatus according to claim 7, further comprising one or more controls selected from the group consisting of frequency, voltage, and duration controls for an energy source used to excite said piezoelectric transducer and thereby propagate an acoustic wave therefrom.

9. An apparatus according to claim 1 or claim 2, further comprising a fluid level detector adapted to detect a level or volume of fluid in the source fluid containment structure.

10. An apparatus according to claim 9, wherein said acoustic liquid deposition emitter further comprises a transducer for generating an acoustic wave and a lens in operative association with the transducer for focusing the acoustic wave emitted by the transducer; said apparatus further comprising:
    a coupling liquid interposed between the lens and the source fluid containment structure; and
    a computer in operable communication with the acoustic liquid deposition emitter, wherein the computer comprises a computer implemented algorithm for adjusting the frequency of the acoustic wave.

11. An apparatus according to claim 9, wherein said acoustic liquid deposition emitter further comprises a transducer for generating an acoustic wave and a lens in operative association with the transducer for focusing the acoustic wave emitted by the transducer; and further comprising:
    a coupling liquid interposed between the lens and the source fluid containment structure; and
    a computer in operable communication with the acoustic liquid deposition emitter, wherein the computer comprises a computer implemented algorithm for adjusting the voltage used to excite the acoustic liquid deposition emitter.

12. An apparatus according to claim 9, wherein said acoustic liquid deposition emitter further comprises a transducer for generating an acoustic wave and a lens in operative association with the transducer for focusing the acoustic wave emitted by the transducer; and farther comprising:
    a coupling liquid interposed between the lens and the source fluid containment structure; and
    a computer in operable communication with the acoustic liquid deposition emitter, wherein the computer comprises a computer implemented algorithm for adjusting the duration of energy used to excite the acoustic liquid deposition emitter.

13. An apparatus according to claim 9, wherein said acoustic liquid deposition emitter further comprises a transducer for generating an acoustic wave and a lens in operative association with the transducer for focusing the acoustic wave emitted by the transducer; and further comprising:
    a coupling liquid interposed between the lens and the source fluid containment structure; and
    a computer in operable communication with the acoustic liquid deposition emitter, wherein the computer comprises a computer implemented algorithm for adjusting the location of the stage relative to the acoustic deposition emitter in response to a change in fluid level or volume detected by the fluid level detector.

14. An apparatus according to claim 1 or claim 2, wherein:
said source fluid containment structure comprises a first well containing a first liquid.

15. An apparatus according to claim 14, wherein:
at least one of the acoustic liquid deposition emitter and the stage is adapted to move so that a distance between the acoustic liquid deposition emitter and the first well is variable.

16. An apparatus according to claim 15, further comprising:
    a translator adapted to maintain a distance between the acoustic liquid deposition emitter and a surface of the first liquid as the volume of the first liquid iii the first well decreases.

17. An apparatus according to claim 15, wherein:
said acoustic liquid deposition emitter is adapted to move to compensate as the level of the first liquid changes in the first well.

18. An apparatus according to claim 15, wherein:
said stage is adapted to move to compensate as the level of the first liquid changes in the first well.

19. An apparatus according to claim 15, wherein:
the acoustic liquid deposition emitter comprises a piezoelectric transducer that generates acoustic energy and a lens that focuses the acoustic energy toward the surface of the first liquid.

20. An apparatus according to claim 14, wherein:
said source fluid containment structure further comprises a second well adjacent to the first well; and
said stage is adapted to move so that the second well is positionable in sufficient proximity to the acoustic liquid deposition emitter that acoustic energy from the acoustic liquid deposition emitter propels a portion of a volume of a second liquid from the second well.

21. An apparatus according to claim 20, wherein:
said first well and said second well form a portion of a multiwell plate.

22. An apparatus according to claim 1 or claim 2, further comprising:
a reservoir configured to hold the coupling liquid interposed between the acoustic liquid deposition emitter and the source fluid containment structure for transmitting acoustic energy therebetween.

23. An apparatus according to claim 1 or claim 2, wherein:
said source fluid containment structure comprises a first well for holding a first liquid, said first well being adapted to be removed from the stage.

24. An apparatus according to claim 23, wherein:
said first well forms a portion of a multiwell plate.

25. An apparatus according to claim 1, or claim 2, wherein:
said acoustic liquid deposition emitter has a curved surface for contacting the coupling liquid to form a lens which focuses acoustic energy from the acoustic liquid deposition emitter toward a surface of a liquid contained in the source fluid containment structure.

26. An apparatus according to claim 1 or claim 2, further comprising:
an actuator for positioning the stage.

27. An apparatus according to claim 26, further comprising:
a computer in operable communication with the actuator, wherein the computer comprises a computer implemented algorithm for controlling the positioning of the stage.

28. An apparatus according to claim 1 or clam 2, further comprising:
a biological compound contained within the source fluid containment structure.

29. An apparatus according to claim 28, wherein:
said biological compound comprises a nucleic acid, a peptide, a polypeptide, a eukaryotic cell, a prokaryotic cell, a carbohydrate, or a combination thereof.

30. An apparatus according to claim 28, wherein:
said biological compound comprises a mono- or oligonucleotide, or combination thereof.

31. An apparatus according to claim 30, wherein said oligonucleotide comprises 2 to 10 nucleotide bases.

32. An apparatus according to claim 30, wherein said oligonucleotide comprises 5 nucleotide bases.

33. An apparatus according to claim 28, Thither comprising:
a for binding one or more source materials.

34. An apparatus according to claim 33, said target bears one or more target materials.

35. An apparatus according to claim 34, wherein said target materials comprise biological or chemical compounds.

36. An apparatus according to claim 35, wherein said target materials comprise a polypeptide, an antibody, an enzyme, or an immunogen.

37. An apparatus according to claim 1 or claim 2, further comprising:
a chemical compound contained within the source fluid containment structure.

38. An apparatus according to claim 37, wherein:
said chemical compound comprises a dye, a detectable label, a non-enzyme chemical reagent, or a diluent.

39. An apparatus according to claim 1 or claim 2, wherein:
said acoustic liquid deposition emitter is adapted to generate an acoustic wave causing ejection of at least one droplet of source fluid contained in the source fluid containment structure, said at least one droplet having a diameter of less than about 10,000 micrometers.

40. An apparatus according to claim 1 or claim 2, wherein:
said acoustic liquid deposition emitter is adapted to generate an acoustic wave causing ejection of at least one droplet of source fluid contained in the source fluid containment structure, said at least one droplet having a diameter in the range of about 1 micrometer to about 10,000 micrometers.

41. An apparatus according to claim 1 or claim 2, wherein:
said acoustic liquid deposition emitter is adapted to generate an acoustic wave causing ejection of at least one droplet of source fluid contained in the source fluid containment structure, said at least one droplet having a diameter in the range of about 500 micrometers to about 1,000 micrometers.

42. An apparatus according to claim 1 or claim 2, wherein:
said acoustic liquid deposition emitter is adapted to generate an acoustic wave causing ejection of at least one droplet of source fluid contained in the source fluid containment structure, said at least one droplet having a diameter in the range of about 60 micrometers to about 500 micrometers.

43. An apparatus according to claim 1 or claim 2, wherein:
said acoustic liquid deposition emitter is adapted to generate an acoustic wave causing ejection of at least one droplet of source fluid contained in the source fluid containment structure, said at least one droplet having a diameter in the range of about 120 micrometers to about 250 micrometers.

44. An apparatus according to claim 1 or claim 2, wherein:
said acoustic liquid deposition emitter is adapted to generate an acoustic wave causing ejection of at least one droplet of source fluid contained in the source fluid containment structure, said at least one droplet having a diameter in the range of about 30 micrometers to about 60 micrometers.

45. An apparatus according to claim 11, wherein:
an acoustic wave emitted by said acoustic liquid deposition emitter is transmitted through the coupling liquid to the source fluid containment structure and thereafter propagates through the source fluid containment structure into a pool of source fluid contained in the source fluid containment structure, causing controlled ejection of at least one droplet of said source fluid from said pool.

46. An apparatus according to claim 1 or claim 2, wherein the acoustic liquid deposition emitter is stationary.

47. An apparatus according to claim 1 or claim 2, wherein the stage is movable relative to a target.

* * * * *

UNITED STATES PATENT AND TRADEMARK OFFICE
CERTIFICATE OF CORRECTION

PATENT NO. : 6,596,239 B2  Page 1 of 1
DATED : July 22, 2003
INVENTOR(S) : Roger O. Williams et al.

It is certified that error appears in the above-identified patent and that said Letters Patent is hereby corrected as shown below:

Column 19,
Line 31, please delete the word "is".

Column 20,
Line 27, please replace the word "farther" with -- further --.
Line 59, please replace the word "iii" with -- in --.

Column 21,
Line 60, please replace the word "Thither" with -- further --.
Line 62, please replace "a for binding" with -- a target functional for binding --.
Line 63, please replace "33, said target" with -- 33, wherein said target --.

Column 22,
Line 53, please replace "claim 11" with -- claim 1 --.

Signed and Sealed this

Tenth Day of February, 2004

JON W. DUDAS
*Acting Director of the United States Patent and Trademark Office*